United States Patent [19]

Ellames et al.

[11] Patent Number: 4,758,565
[45] Date of Patent: Jul. 19, 1988

[54] SUBSTITUTED PYRIMIDOQUINOXALINES USEFUL AS ANTI-ANAEROBIC AGENTS

[75] Inventors: George J. Ellames; Kevin R. Lawson, both of High Wycombe; Albert A. Jaxa-Chamiec, Marlow; Roger M. Upton, High Wycombe, all of United Kingdom

[73] Assignee: G. D. Searle & Co., Chicago, Ill.

[21] Appl. No.: 897,461

[22] Filed: Aug. 18, 1986

[51] Int. Cl.⁴ .................. A61K 31/505; C07D 487/04
[52] U.S. Cl. ..................................... 514/250; 544/250
[58] Field of Search .......................... 544/250; 514/250

[56] References Cited

U.S. PATENT DOCUMENTS

| | | | |
|---|---|---|---|
| 4,472,401 | 9/1984 | Kennewell et al. | 514/250 |
| 4,510,143 | 4/1985 | Westwood et al. | 514/250 |
| 4,696,928 | 9/1987 | Ellames et al. | 514/250 |

OTHER PUBLICATIONS

Otomasu et al., Chemical Abstracts, vol. 74:53730x, (1971).
Rodway et al., Chemical Abstracts, vol. 77:126598j, (1972).
Otsumasu, Chemical Abstracts, vol. 81:91574b, (1974).
Rodway et al., Chemical Abstracts, vol. 81:13559m, (1974).
Parthasarathy et al., Indian J. Chem., Sect. B, 1983, vol. 22B(12), pp. 1250-1251, (1983).

*Primary Examiner*—Donald G. Daus
*Assistant Examiner*—Diana G. Rivers
*Attorney, Agent, or Firm*—Frank P. Grassler; Paul D. Matukaitis

[57] ABSTRACT

This disclosure relates to a novel class of substituted quinoxaline derivatives. The disclosure further relates to pharmaceutical compositions containing such compounds and to the use of such compounds and compositions as anti-anaerobic agents.

20 Claims, No Drawings

4,758,565

SUBSTITUTED PYRIMIDOQUINOXALINES USEFUL AS ANTI-ANAEROBIC AGENTS

This invention relates to a novel class of substituted pyrimidoquinoxaline derivatives. The present invention further relates to pharmaceutical compositions containing such compounds and to the use of such compounds and compositions as anti-anaerobic agents.

BACKGROUND OF THE INVENTION

Parthasarathy, et al., Indian Journal of Chemistry, 22B, 1250–1251 (1983), describe a class of substituted 1,2-dihydroimidazo[1,2-a]quinoxaline 5-oxides that have antiamoebic activity against Entamoeba histolytica in intestinal and hepatic amoebiasis. Parthasarathy, et al., Indian Journal of Chemistry, 22B, 1233–1235 (1983), describe certain N-oxides of 2,3-dihydro-1H-pyrimido[2,1-h]pteridines; 1,2-dihydroimidazo[2,1-h]pteridines; 10-aza-2,3-dihydro-1H-pyrimido[1,2-a]quinoxalines; 9-aza-1,2-dihydroimidazo[1,2-a]quinoxalines and 7-aza-1,2-dihydroimidazo[1,2-a]quinoxalines which possess antiamoebic activity, in particular against hepatic amoebiasis. Strauss, et al., J. Org. Chem., 43, 2041–2044 (1978), describe the preparation of quinoxaline and dihydroimidazoquinoxaline N-oxides.

SUMMARY OF THE INVENTION

The present invention relates to a class of novel compounds of the formula

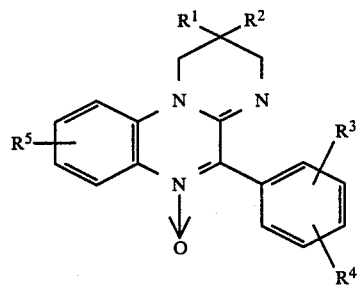

wherein p0 $R^1$ and $R^2$ are independently hydrogen or $C_1$–$C_6$ alkyl;
$R^3$ and $R^4$ are independently selected from the class consisting of hydrogen, halo, $C_1$–$C_6$ alkyl, and $C_1$–$C_6$ alkoxy;
$R^5$ is halo or trifluoromethyl;
and pharmaceutically acceptable salts thereof.

The present invention further relates to pharmaceutical compositions containing such compounds and to the use of such compounds as anti-anaerobic agents.

The term "$C_1$–$C_6$ alkyl" groups specified herein includes straight chain or branched chain hydrocarbon groups having from one to six carbon atoms respectively. Illustrative of such alkyl groups are methyl, ethyl, propyl, isopropyl, butyl, isobutyl, sec-butyl, tert-butyl, pentyl, neopentyl, hexyl, isohexyl, and the like.

The term "$C_1$–$C_6$ alkoxy" groups specified herein includes straight chain or branched chain alkoxy groups having from one to six carbon atoms respectively. Representative of such groups include, for example, methoxy, ethoxy, propoxy, isopropoxy, butoxy, t-butoxy, pentoxy, hexoxy and the like.

As used herein the term "halogen or halo" refers to fluoro, chloro, iodo and bromo.

DETAILED DESCRIPTION OF THE INVENTION

The compounds of the present invention may be prepared in accordance with the following general procedure:

A substituted tetrahydrophenylmethylpyrimidine of the formula

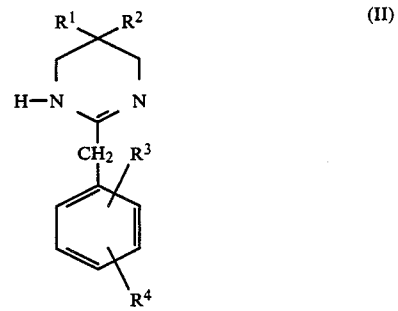

wherein $R^1$, $R^2$, $R^3$ and $R^4$ are as above defined; is reacted with a substituted nitroaromatic of the formula

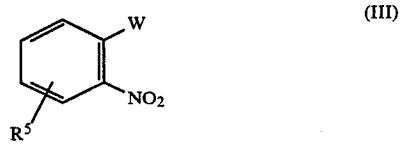

wherein W is halo and $R^5$ is above defined; under basic conditions in an appropriate solvent, such as isopropyl alcohol or acetonitrile, to yield a dihydropyrimido[1,2-a]quinoxaline of the formula:

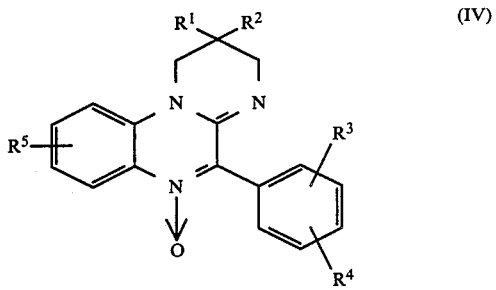

The pharmaceutically acceptable salts of the compounds of formula (IV) may be prepared by conventional procedures, such as by reacting the free base in a suitable solvent, e.g. diethylether or ethanol, with a solution containing one equivalent of the desired acid in a suitable solvent, e.g. diethylether or ethanol. The salt generally preciptates from solution or is recovered by evaporation of the solvent. Such pahrmaceutically acceptable salts include, for example, hydrochloride, sulfate, phospahte and the like.

A preferred embodiment includes compounds of the formula

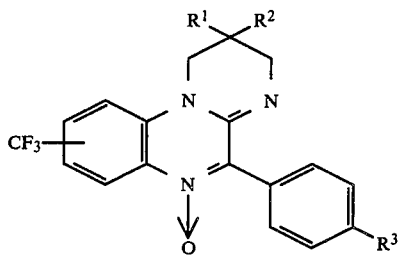

wherein R[1], R[2] and R[3] are above defined.

A more preferred embodiment encompasses compounds of formula (V) wherein R[1] and R[2] are $C_1$-$C_6$ alkyl and R[3] is hydrogen, and most preferred are compounds of formula (V) wherein R[1] and R[2] are methyl.

The appropriate solvents employed in the above reactions are solvents in which the reactants are soluble but do not react with the reactants. The preferred solvents vary from reaction to reaction and are readily ascertained by one of ordinary skill in the art.

The compounds of the present invention may be administered by any suitable route, preferably in the form of a pharmaceutical composition adapted to such a route and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit contained in a particular amount of the active ingredient. Examples of such dosage units are tablets or capsules. These may with advantage contain an amount of active ingredient of about 1 to 250 mg, preferably about 25 to 150 mg. A suitable daily dose for a mammal may vary widely depending on the condition of the patient and other factors. However, a dose of about 0.1 to 300 mg/kg body weight, particularly of about 1 to 100 mg/kg body weight, may be appropriate.

The active ingredient may also be administered by injection as a composition wherein, for example, saline, dextrose or water may be used as a suitable carrier. A suitable daily dose is about 0.1 to 100 mg per kg body weight injected per day in multiple doses depending on the disease being treated. A preferred daily dose would be about 1 to 30 mg/kg body weight.

The dosage regimen for treating an infectious disease condition with the compounds and/or compositions of this invention is selected in accordance with a variety of factors, including the type, age, weight, sex and medical condition of the patient; the severity of the infection; the route of administration; and the particular compound employed and thus may vary widely.

For therapeutic purposes, the compounds of this invention are ordinarily combined with one or more adjuvants appropriate to the indicated route of administration. If per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and thus tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration and well and widely known in the pharmaceutical art. Appropriate dosages, in any given instance, of course depend upon the nature and severity of the condition treated, the route of administration, and the species of mammal involved, including its size and any individual idiosyncrasies.

Representative carriers, diluents and adjuvants include, for example, water, lactose, gelatin, starches, magnesium stearate, talc, vegetable oils, gums, polyalkylene glycols, petroleum jelly, etc. The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

As previously mentioned, the compounds and compositions of the present invention are effective as anti-anaerobic agents for the treatment of infectious diseases related to anaerobic bacteria. Representative of infectious diseases that may be treated with the compounds and compositions of the present invention include, for example, post operative sepsis following lower gastrointestinal surgery or female urinogenital surgery, pelvic inflammatory disease, ulcers, gangrene, trichomonal vaginitis, non-specific vaginitis, amoebiasis, giardiasis, periodontal disease, acne and the like.

The following Examples are intended to further illustrate the present invention and not to limit the invention in spirit or scope. In the Examples, all parts are parts by weight unless otherwise expressly set forth.

EXAMPLE 1

2,3-Dihydro-2,2-dimethyl-5-phenyl-8-trifluoromethyl-1H-pyrimido[1,2-a]quinoxaline 6-oxide A mixture of 1,4,5,6-tetrahydro-5,5-dimethyl-2-phenylmethylpyrimidine (1.69, 8 mmol), 1-fluoro-2-nitro-4-trifluoromethylbenzene (1.679, 8 mmol) and potassium carbonate (550 mg, 4 mmol) in acetonitrile (25 ml) was heated overnight at 40° C. The solvent was removed in vacuo and the resulting yellow solid recrystallised from ethyl acetate to yield 2,3-dihydro-2,2-dimethyl-5-phenyl-8-trifluoromethyl-1H-pyrimido[1,2-a]quinoxaline 6-oxide (800 mg) as a yellow crystalline solid, m.p. 225°–227° C. (Found: C, 64.42, H, 4.95, N, 11.23%; $C_{20}H_{18}F_3N_3O$ requires C, 64.34, H, 4.86, N, 11.25%) and represented by the structural formula:

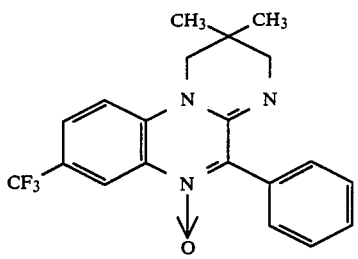

EXAMPLES 2–9

The following compounds were prepared in accordance with the procedure of Example 1 utilizing the appropriately substituted nitrobenzene and tetrahydropyrimidine.

EXAMPLE 2

2,3-Dihydro-2,2-dimethyl-9-fluoro-5-phenyl-1H-pyrimido [1,2-a]quinoxaline 6-oxide yellow crystalline solid, m.p. 206°–209° C., (Found: C, 69.58, H, 5.53, N, 13.04%; $C_{19}H_{18}FN_3O \cdot 0.2H_2O$ requires C, 69.81, H, 5.63, N, 12.86%) represented by the structural formula:

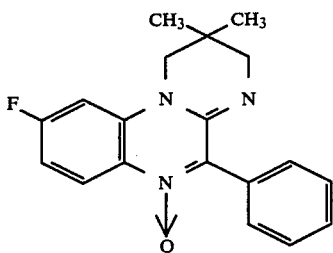

EXAMPLE 3

2,3-Dihydro-2,2-dimethyl-5-(4-methylphenyl)-8-trifluoromethyl-1H-pyrimid [1,2-a]quinoxaline 6-oxide yellow cyrstalline solid, m.p. 235°–237° C., (Found: C, 65.30, H, 5,32, N, 10.80%; $C_{21}H_{20}F_3N_3O$ requires C, 65.11, H, 5.20 N, 10.85%) represented by the structural formula:

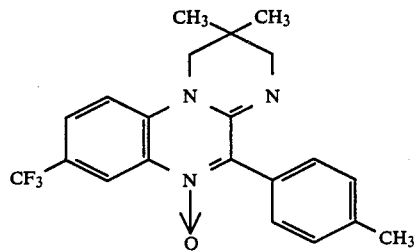

EXAMPLE 4

2,3-Dihydro-2-ethyl-2-methyl-5-phenyl-8-trifluoromethyl-1H-pyrimido [1,2-a]quinoxaline 6-oxide yellow cyrstalline solid, m.p. 185°–187° C., (Found: C, 65.03, H, 5.26, N, 10.81%; $C_{21}H_{20}N_3O_F$ requires C, 65.11, H, 5.20 N, 10.85%) represented by the structural formula:

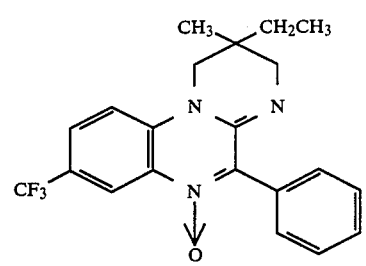

EXAMPLE 5

2,3-Dihydro-2,2-dimethyl-10-fluoeo-5-phenyl-1H-pyrimido [1,2-a]quinoxaline 6-oxide yellow cyrstalline solid, m.p. 191°–193° C., (Found: C, 70.60, H, 5.62, N, 12.99%; $C_{19}H_{18}FN_3O$ requires C, 70.57, H, 5.61, N,12.99%) represented by the structural formula:

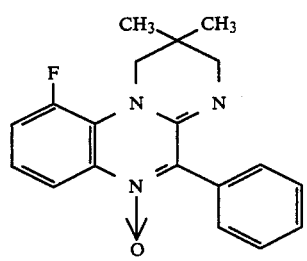

EXAMPLE 6

2,3-Dihydro-2-ethyl-2-methyl-5-(4-methylphenyl)-8-trifluoromethyl-1H-pyrimdo [1,2-a]quinoxaline 6-oxide yellow crystalline solid, m.p. 173°–175° C., (Found C, 64.46, H, 5.36, N, 10.47%; $C_{22}H_{22}F_3N_3O \cdot 0.5H_2O$ requires C, 64.38, H, 5.65, N, 10.24%) represented by the structural formula;

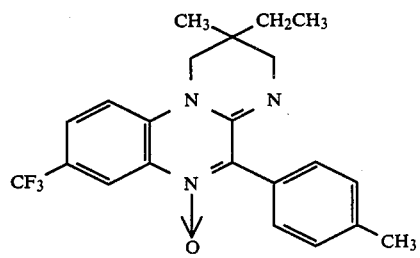

EXAMPLE 7

2,3-Dihydro-2,2-dimethyl-5-(4-methylphenyl)-8-trifluoromethyl-1H-pyrimdo [1,2-a]quinoxaline 6-oxide yellow crystalline solid, m.p. 222°–224° C., (Found: C 61.11 H, 4.31, N, 10.88%; $C_{20}H_{17}F_4N_3O$ requires C, 61.38, H, 4.38, N, 10.74%) represented by the structural formula:

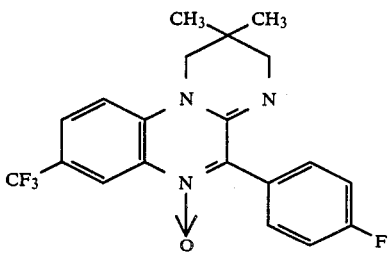

EXAMPLE 8

2,3-Dihydro-2,2-dimethyl-5-phenyl-8-trifluoromethyl-1H-pyrimdo [1,2-a]quinoxaline 6-oxide yellow crystalline solid, m.p. 161°–163° C., (Found: C, 66.04, H, 5.60, N, 10.46%; $C_{22}H_{22}F_3N_3O$ requires C, 65.82, H, 5.52, N, 10.47%) represented by the structural formula:

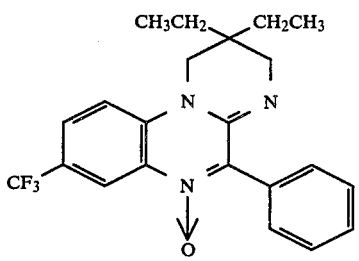

EXAMPLE 9

2,3-Dihydro-2,2-dipropyl-5-phenyl-8-trifluoromethyl-1H-pyrimido[1,2-a]quinoxaline 6-oxide:

yellow crystalline solid. m.p. 169°–171° C., (Found: C, 67.09, H, 6.08, N, 9.70%; $C_{24}H_{26}F_3N_3O$ requires C, 67.12, H, 6.10, N, 9.78%) represented by the structural formula:

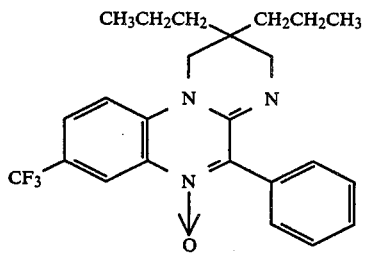

EXAMPLE 10

2,3-Dihydro-2,2-dimethyl-5-phenyl-8-trifluoromethyl-1H-pyrimido[1,2-a]quinoxaline 6-oxide hydrochloride 2,3-Dihydro-2,2-dimethyl-5-phenyl-8-trifluoromethyl-1H-pyrimido[1,2-a]quinoxaline 6-oxide (70 g) was suspended in ethanol (500 ml) and cooled in an ice-bath. Gaseous hydrogen chloride was passed through the suspension until all solid had dissolved. The solvent was then removed in vacuo and the resulting solid recrystallized from hot ethyl acetate to yield 57.87 g of 2,3-dihydro-2,2-dimethyl-5-phenyl-8-trifluoromethyl-1H-pyrimido[1,2-a]quinoxaline 6-oxide hydrochloride as a bright yellow crystalline solid, m.p. 234° C., (Found: C, 58.43, H, 4.68, N, 10.15%; $C_{20}H_{19}ClF_3N_3O$ requires C, 58.61, H, 4.67, N, 10.25%) and represented by the structural formula:

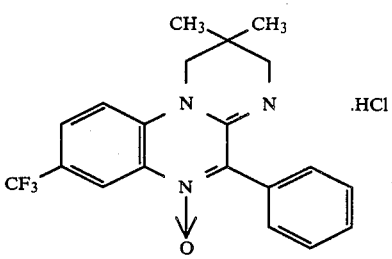

EXAMPLE 11

The screening panel utilized in this example consisted of 5 strains of *Bacteroides fragilis*. All assays were carried out in 96-well microtitre plates. If an isolate was obtained from either a culture collection or clinical source, the isolate was immediately inoculated into Wilkins-Chalgren broth (Oxoid) and incubated at 37° C. in an anaerobic chamber in an atmosphere of 85% nitrogen, 10% carbon dioxide, and 5% hydrogen for 48 hours. At the end of this time, the viable count was about $10^{12}$ organisms/ml broth. A 1 ml aliquot of each culture was placed in an ampoule and quick frozen in acetone-dry ice mixture and stored in liquid nitrogen. When an inoculum was utilised in an assay, one of the ampoules was thawed and diluted with fresh broth to yield a suspension having a count of $5 \times 10^5$ organisms/ml A 100 μl aliquot of the suspension was inoculated into each well of the microtitre plate.

A 2 mg sample of the test compound was dissolved in 0.2 ml of a suitable solvent such as dimethylsulfoxide, polyethylene glycol 200 or methanol. The solution was then diluted with 4.8 ml of water to yield a solution having a concentration of 400 mg/L. Doubling dilutions of this stock were prepared to give a range of concentrations from 1.6–200 mg/L. 100 μl of each concentration were then placed in the wells of the microtitre plate containing the inoculum, to produce a mixture having a final concentration in the range of 0.8–100 mg/L. Metronidazole was employed as a positive control and a solvent/water mixture was employed as a negative control. After addition of the test solution the final inoculum level was 105 cells/ml. The plates were incubated for 48 hours at 37° C. in the anaerobic chamber. The Minimum Inhibitory Concentration (MIC) was read visually. The MIC is defined as the lowest concentration at which there is no detectable growth. The Minimum Bactericidal Concentration (MBC) was determined by taking 50 μl aliquot from each well and placing it in fresh medium. The MBC is defined as the lowest concentration at which there are less than 5 colonies (i.e. 99.9% reduction in viable count) after 48 hours of incubation. The MIC and MBC values for each compound tested and the respective MIC and MBC value for metronidazole are indicated in Table 1. The MIC and MBC value for the negative control that was assayed along with each test compound was greater than 100 mg/L. The MIC and MBC values in Table 1 are expressed in mg/L. A blank in the table represented by a "-" indicates that the assay was not conducted using the strain indicated.

The strains of *Bacteroides fragilis* utilized in the above procedure are identified by letter in accordance with the following legend:

| Strain | |
|---|---|
| A | *B. fragilis* NCTC 10581 |
| B | *B. fragilis* NCTC 9353 |
| C | *B. fragilis* NCTC 9344 |
| D | *B. fragilis* MZ-R ATCC 11295 |
| E | *B. fragilis* WS-1* |

*Obtained from St. Thomas's Hospital Medical School, London, United Kingdom.

TABLE 1

| COMPOUND OF EXAMPLE NO. | STRAIN | | | | | | | | | |
|---|---|---|---|---|---|---|---|---|---|---|
| | A | | B | | C | | D | | E | |
| | MIC | MBC | MIC | MBC | MIC | MBC | MIC | MBC | MIC | MBC |
| 1 | 3.1 | 3.1 | 1.5 | 1.5 | 1.5 | 3.1 | 0.8 | 0.8 | 1.5 | 1.5 |
| Metronidazole | <0.8 | <0.8 | <0.8 | <0.8 | <0.8 | 1.5 | 6.2 | 6.2 | 3.1 | 3.1 |
| 2 | — | — | <0.8 | <0.8 | <0.8 | 1.5 | <0.8 | <0.8 | <0.8 | <0.8 |
| Metronidazole | — | — | <0.8 | <0.8 | <0.8 | <0.8 | 12.5 | 12.5 | <0.8 | <0.8 |
| 3 | <0.8 | <0.8 | 1.5 | 1.5 | 3.1 | 3.1 | 1.5 | 6.2 | <0.8 | 1.5 |
| Metronidazole | <0.8 | <0.8 | <0.8 | <0.8 | <0.8 | <0.8 | 12.5 | 12.5 | <0.8 | <0.8 |
| 4 | <0.8 | 1.5 | <0.8 | <0.8 | <0.8 | <0.8 | <0.8 | <0.8 | <0.8 | <0.8 |
| Metronidazole | <0.8 | <0.8 | <0.8 | <0.8 | <0.8 | <0.8 | 12.5 | 12.5 | <0.8 | <0.8 |
| 5 | <0.8 | 1.5 | <0.8 | <0.8 | <0.8 | <0.8 | <0.8 | <0.8 | <0.8 | <0.8 |
| Metronidazole | <0.8 | <0.8 | <0.8 | <0.8 | <0.8 | <0.8 | 12.5 | 12.5 | <0.8 | <0.8 |
| 6 | 6.2 | 6.2 | 6.2 | 6.2 | 3.1 | 3.1 | 1.5 | 3.1 | 3.1 | 3.1 |
| Metronidazole | <0.8 | <0.8 | 1.5 | 1.5 | <0.8 | 1.5 | 12.5 | 12.5 | 1.5 | 1.5 |

EXAMPLE 12

Utilizing the procedures described in Example 11, the anti-anaerobic activity of certain compounds of the present invention was demonstrated utilizing an additional 10 stains of various anaerobic bacteria.

The MIC values obtained are indicated in Table 2. A blank in the table represented by a "-" indicates that the assay was not conducted using the strain indicated.

TABLE 2

MIC vs PANEL OF ANAEROBES

| ORGANISM | COMPOUND OF EXAMPLE NO. | | |
|---|---|---|---|
| | (1) | (2) | (3) |
| *Clostridium perfringens* NCTC 523 | 1.5 | 3.1 | <0.8 |
| *Clostridium difficile* NCIB 10666 | <0.8 | 3.1 | <0.8 |
| *Campylobacter fetus ss. jejuni* ATCC 29428 | 100 | 25 | >100 |
| *Campylobacter fetus ss. jejuni* NCTC 10842 | >100 | 50 | 12.5 |
| *Fusobacterium necrophorum* ATCC 25286 | — | <0.8 | <0.8 |
| *Fusobacterium necrophorum* ATCC 11295 | 1.5 | 3.1 | 6.2 |
| *Bacteroides melanogenicus* NCTC 9336 | >100 | 50 | >100 |
| *Peptococcus magnus* | — | <0.8 | >100 |
| *Peptostreptococcus anaerobius* | 100 | 1.5 | >100 |
| *Propionebacterium acnes* NCTC 7337 | 100 | 50 | >100 |

EXAMPLE 13

Determination of in vivo Anti-anaerobe activity—mouse hepatic necrosis 500 ml volumes of basic anaerobe broth (nutrient broth No. 2 (LAB M) 28 g/L, haemin 5 mg/L, vitamin K 0.5 mg/L, and cysteine hydrochloride 0.5 g/L) were inoculated from a cooked meat broth stock culture of *B. fragilis* 23745 which had been inoculated from the original cooked meat broth stock so that subculturing was kept to a minimum. Cultures were incubated anaerobically in an anaerobic chamber. When the broths reached a heavy turbidity (24–48 hours), they were aliquoted into small bottles to which inactivated horse serum was added to 10%, together with a few drops of neutralised ascorbate (100 mg/ml), before snap freezing and storing at $-20°$ C. The viable count was $10^{10}$ organisms/ml.

Rat faeces or mouse bowel contents were mixed with a small volume of water and autoclaved, then homogenised. After standing overnight, they were autoclaved again and then freeze-dried in small batches.

Stock inoculum was thawed and diluted with fresh broth to yield a viable count of $5 \times 10^8$ organisms/ml, and sterile faecal material was added to a final concentration of 2% w/v. Animals (groups of ten male BALB/c mice weighing 18–22 g) were inoculated intraperitoneally with 0.2 ml of the inoculum so that each receives $10^8$ *B. fragilis* organisms.

Test compounds were dissolved in polyethylene glycol 200 or dimethylsulfoxide and then diluted with water or saline to give the appropriate final concentration. The stock solution was used to prepare a two-fold dilution series having a final dose range of 2.5–40 mg/kg. The initial dose was given p.o. immediately after infection and twice daily thereafter for 2 days. Animals were sacrificed on the third day using carbon dioxide or cervical dislocation. Control animals received dosing vehicle only. Metronidazole was used as a positive control.

At the end of the experimental period the animals' livers were removed aseptically with care not to puncture the bowel and transferred to Universal bottles of peptone water and kept on ice. The livers were homogenized at low speed with care to prevent frothing, and the bottles were gassed out again. Homogenate was diluted by transferring 0.1 ml of the homogenate to a 10 ml aliquot of peptone water diluent, and the diluted homogenate was spread on basic anaerobic agar at 0.1 ml per petri-dish. The media used for this purpose must have either been prepared freshly, or stored in plastic bags in which the air has been replaced by anaerobic gas mixture, or stored in anaerobic jars. After the homogenate was spread on the petri-dish, the petri-dishes were left exposed to air for the minimum possible time (and never more than 15 minutes) so that small numbers of Bacteroides were recovered and grown from the inoculum.

Cultures were incubated anaerobically for 48 hours in a Form Anaerobic Chamber at 37° C. At the end of this period, the resultant colonies were counted using an AMS 40–10 Image Analyser. The mean number of viable organisms were calculated for each treatment group and the data analysed using analysis of varience and two sample t-test for comparison of individual groups. Results were expressed as the reduction in log colony forming units/ml of liver homogenate for each treatment group compared to the untreated controls. From the dose response curves, the dose giving 1 log (90%) reduction is calculated for each compound and the efficacy of the test compound relative to metronidazole is determined.

Under these test conditions, metronidazole gives a reduction in *B. fragilis* of 3–3.5 $\log_{10}$ at 40 mg/kg (p.o).

The activities of the compounds described above are given in Table 3.

TABLE 3

| COMPOUND OF EXAMPLE NO. | DOSE GIVING 1 LOG REDUCTION mg/kg ($\mu$M/Kg) | |
|---|---|---|
| | | METRONIDAZOLE |
| (1) | 2.05 (5.5) | 1.9 (11.0) |
| (2) | 2.7 (8.4) | 1.9 (11.2) |
| (3) | 22.6 (58.0) | 3.1 (18.4) |
| (4) | 4.45 (11.5) | 3.1 (18.4) |
| (5) | 3.2 (9.9) | 3.4 (19.8) |

Although this invention has been described with respect to specific modification, the details thereof are not to be construed as limitations, for it will be apparent that various equivalents, changes and modifications may be resorted to without departing from the spirit and scope thereof and it is understood that such equivalent embodiments are intended to be included therein.

What is claimed is:

1. A compound of the formula

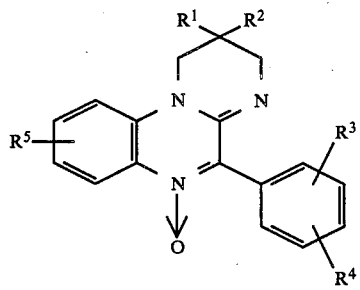

wherein
$R^1$ and $R^2$ are independently $C_1$–$C_6$ alkyl;
$R^3$ and $R^4$ are independently selected from the class consisting of hydrogen, halo, $C_1$–$C_6$ alkyl, and $C_1$–$C_6$ alkoxy;
$R^5$ is halo or trifluoromethyl;
and pharmaceutically acceptable salts thereof.

2. A compound according to claim 1 wherein $R^1$ and $R^2$ are $C_1$–$C_6$ alkyl.

3. A compound according to claim 2 wherein $R^5$ is trifluoromethyl.

4. A compound according to claim 3 wherein $R^3$ and $R^4$ are hydrogen.

5. A compound according to claim 4 which is 2,3-dihydro-2,2-dimethyl-5-phenyl-8-trifluoromethyl-1H-pyrimido[1,2-a]quinoxaline 6-oxide.

6. A compound according to claim 4 which is 2,3-dihydro-2-ethyl-2-methyl-5-phenyl-8-trifluoromethyl-1H-pyrimido[1,2-a]quinoxaline 6-oxide.

7. A compound according to claim 4 which is 2,3-dihydro-2,2-diethyl-5-phenyl-8-trifluoromethyl-1H-pyrimido[1,2-a]quinoxaline 6-oxide.

8. A compound according to claim 4 which is 2,3-dihydro-2,2-dipropyl-5-phenyl-8-trifluoromethyl-1H-pyrimido[1,2-a]quinoxaline 6-oxide.

9. A compound according to claim 3 wherein $R^3$ is $C_1$–$C_6$ alkyl and $R^4$ is hydrogen.

10. A compound according to claim 9 which is 2,3-dihydro-2,2-dimethyl-5-(4-methylphenyl)-8-trifluoromethyl-1H-pyrimido[1,2-a]quinoxaline 6-oxide.

11. A compound according to claim 9 which is 2,3-dihydro-2-ethyl-2-methyl-5-(4-methylphenyl)-8-trifluoromethyl-1H-pyrimido[1,2-a]quinoxaline 6-oxide.

12. A compound according to claim 3 wherein $R^3$ is halo and $R^4$ is hydrogen.

13. A compound according to claim 12 which is 2,3-dihydro-2,2-dimethyl-5-(4-fluorophenyl)-8-trifluoromethyl-1H-pyrimido[1,2-a]quinoxaline 6-oxide.

14. A compound according to claim 2 wherein $R^5$ is halo.

15. A compound according to claim 14 which is 2,3-dihydro-2,2-dimethyl-9-fluoro-5-phenyl-1H-pyrimido[1,2-a]quinoxaline 6-oxide.

16. A compound according to claim 14 which is 2,3-dihydro-2,2-dimethyl-10-fluoro-5-phenyl-1H-pyrimido[1,2-a]quinoxaline 6-oxide.

17. A pharmaceutical composition comprising at least one compound according to claim 1, together with one or more non-toxic pharmaceutically acceptable carriers.

18. A pharmaceutical composition according to claim 17 wherein said compound is selected from the group consisting of:
2,3-dihydro-2,2-dimethyl-5-phenyl-8-trifluoromethyl-1H-pyrimido[1,2-a]quinoxaline 6-oxide,
2,3-dihydro-2-ethyl-2-methyl-5-phenyl-8-trifluoromethyl-1H-pyrimido[1,2-a]quinoxaline 6-oxide,
2,3-dihydro-2,2-diethyl-5-phenyl-8-trifluoro-methyl-1H-pyrimido[1,2-a]quinoxaline 6-oxide,
2,3-dihydro-2,2-dipropyl-5-phenyl-8-trifluoromethyl-1H-pyrimido[1,2-a]quinoxaline 6-oxide,
2,3-dihydro-2,2-dimethyl-5-(4-methylphenyl)-8-trifluoromethyl-1H-pyrimido[1,2-a]quinoxaline 6-oxide,
2,3-dihydro-2-ethyl-2-methyl-5-(4-methylphenyl)-8-trifluoromethyl-1H-pyrimido[1,2-a]quinoxaline 6-oxide,
2,3-dihydro-2,2-dimethyl-5-(4-fluorophenyl)-8-trifluoromethyl-1H-pyrimido[1,2-a]quinoxaline 6-oxide,
2,3-dihydro-2,2-dimethyl-9-fluoro-5-phenyl-1H-pyrimido[1,2-a]quinoxaline 6-oxide, and
2,3-dihydro-2,2-dimethyl-10-fluoro-5-phenyl-1H-pyrimido[1,2-a]quinoxaline 6-oxide.

19. A method for treating anaerobic infections in mammals comprising administering a therapeutically effective dose of at least one compound of claim 1 to a mammal in need of such treatment.

20. A method according to claim 19 wherein said compound is selected from the group consisting of:
2,3-dihydro-2,2-dimethyl-5-phenyl-8-trifluoromethyl-1H-pyrimido[1,2-a]quinoxaline 6-oxide,
2,3-dihydro-2-ethyl-2-methyl-5-phenyl-8-trifluoromethyl-1H-pyrimido[1,2-a]quinoxaline 6-oxide,
2,3-dihydro-2,2-diethyl-5-phenyl-8-trifluoromethyl-1H-pyrimido[1,2-a]quinoxaline 6-oxide,
2,3-dihydro-2,2-dipropyl-5-phenyl-8-trifluoromethyl-1H-pyrimido[1,2-a]quinoxaline 6-oxide,
2,3-dihydro-2,2-dimethyl-5-(4-methylphenyl)-8-trifluoromethyl-1H-pyrimido[1,2-a]quinoxaline 6-oxide,
2,3-dihydro-2-ethyl-2-methyl-5-(4-methylphenyl)-8-trifluoromethyl-1H-pyrimido[1,2-a]quinoxaline 6-oxide,
2,3-dihydro-2,2-dimethyl-5-(4-fluorophenyl)-8-trifluoromethyl-1H-pyrimido[1,2-a]quinoxaline 6-oxide,
2,3-dihydro-2,2-dimethyl-9-fluoro-5-phenyl-1H-pyrimido[1,2-a]quinoxaline 6-oxide, and
2,3-dihydro-2,2-dimethyl-10-fluoro-5-phenyl-1H-pyrimido[1,2-a]quinoxaline 6-oxide.

* * * * *

UNITED STATES PATENT AND TRADEMARK OFFICE
CERTIFICATE OF CORRECTION

PATENT NO. : 4,758,565
DATED : July 19, 1988
INVENTOR(S) : Ellames, et. al.

It is certified that error appears in the above-identified patent and that said Letters Patent is hereby corrected as shown below:

Column 1, line 45, reading "p0 $R^1$ and $R^2$" should read -- $R^1$ and $R^2$ --.

Column 6, line 61, reading "-(4-methylphenyl)-" should read -- -(4-fluorophenyl)- --.

Column 7, line 15, reading "2-dimethyl-5" should read -- 2-diethyl-5 --.

Column 7, line 39, reading "N, 9.70%;" should read -- N, 9.79%; --.

Signed and Sealed this

Fourteenth Day of November, 1989

Attest:

JEFFREY M. SAMUELS

*Attesting Officer*     *Acting Commissioner of Patents and Trademarks*